(12) United States Patent
Dreyer

(10) Patent No.: US 7,923,040 B2
(45) Date of Patent: Apr. 12, 2011

(54) HOMEOPATHIC FORMULATIONS USEFUL FOR TREATING PAIN AND/OR INFLAMMATION

(75) Inventor: Lee R. Dreyer, Whitefish, MT (US)

(73) Assignee: Nutrition Research, Inc., Eureka, MT (US)

( * ) Notice: Subject to any disclaimer, the term of this patent is extended or adjusted under 35 U.S.C. 154(b) by 772 days.

(21) Appl. No.: 11/677,798

(22) Filed: Feb. 22, 2007

(65) Prior Publication Data

US 2007/0184128 A1    Aug. 9, 2007

Related U.S. Application Data

(62) Division of application No. 10/797,009, filed on Mar. 11, 2004, now Pat. No. 7,229,648.

(60) Provisional application No. 60/454,308, filed on Mar. 14, 2003.

(51) Int. Cl.
*A01N 65/00* (2009.01)
*A61K 31/74* (2006.01)

(52) U.S. Cl. .................. 424/725; 424/78.03; 424/730

(58) Field of Classification Search .................. None
See application file for complete search history.

(56) References Cited

U.S. PATENT DOCUMENTS 6,468,551 B1   10/2002   Diec
7,229,648 B2 *  6/2007   Dreyer

OTHER PUBLICATIONS

Interview with Dr. Frank J. King on Jun. 9, 2005.*
http://www.lifesvigor.com "King Bio Natural Medicines—911 Stress Control 2 oz Liquid" (May 28, 2002) downloaded on Jun. 8, 2005, as evidenced by WayBackMachine at www.archive.org.
http://www.archive.org "Internet Archive Wayback Machine". Search for http://www.kingbio.com/onlinepharmacy.htm. on Jun. 8, 2005.
http://www.homeopathyhome.com/services/rshop/vshoppe/topicals.shtml.
http://web.archive.org/web/*/http://www.homeopathyhome.com/services/rshop/vshoppe/topicals.shtml.
Product Label for Unscented Epicure Crystal Sports Cream, Natural Homeopathic Pain Reliever, 1996.
Product Label for Traumeel, Homeopathic Ointment, 1995.

* cited by examiner

*Primary Examiner* — Michele Flood
(74) *Attorney, Agent, or Firm* — Sughrue Mion, PLLC

(57) ABSTRACT

Homeopathic formulations (a) comprising tinctures and/or diluted extracts preferably subjected to potentization of at least 8 or 9 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*; or (b) consisting of, as active ingredients, tinctures and/or diluted extracts subjected to potentization of 5, 6 or 7 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*. The potentized homeopathics are in a penetrating base, preferably clear gel base. The homeopathic formulations are highly effective in treating or relieving pain and inflammation. Also, a method of treating or relieving pain and inflammation by administering any of the homeopathic formulations of the invention to a subject, preferably a subject in need of such treatment or relief. Further, a method of making the homeopathic formulation by mixing the homeopathically prepared herbal active ingredients with a base, preferably a clear gel base.

8 Claims, No Drawings

HOMEOPATHIC FORMULATIONS USEFUL FOR TREATING PAIN AND/OR INFLAMMATION

This application is a divisional of application Ser. No. 10/797,009 filed on Mar. 11, 2004, now U.S. Pat. No. 7,229, 648, which claims the benefit of U.S. Provisional Patent Application No. 60/454,308, filed on Mar. 14, 2003.

The present invention is related to novel homeopathic over-the-counter (OTC) pain-relieving and/or anti-inflammatory formulations containing (a) 8 or 9 different homeopathic herbal active ingredients described below, (b) 5, 6 or 7 homeopathic herbal active ingredients described below in addition to *Bryonia Alba*, or (c) 5, 6 or 7 homeopathic herbal active ingredients described below excluding *Echinacea Augustifolia* and *Symphytum Officinale*, that can relieve external pain and/or inflammation and that is amenable to self diagnosis and treatment.

BACKGROUND OF THE INVENTION

Currently known OTC analgesic products for topical uses have many problems. There is a need for an OTC topical pain relieving product that relieves most external acute or chronic pain within a few minutes, providing relief that lasts up to several hours (for uninterrupted sleep and work), and without unpleasant physical and social side effects such as strong odors, counterirritation, redness, itching, stinging, cooling, sensitization, staining, burning, perfumes, anesthesia, etc. Ideally such product would also quickly relieve inflammation, edema, redness, and swelling along with pain, thereby increasing pain free range of motion, even in difficult to treat pain cases, without the patient needing strong topical and oral OTC or prescription drugs with powerful undesirable and unpleasant side effects. Currently, most OTC topical pain relief counterirritant products may not be used as frequently as needed because of six problems listed below.

1. The currently available OTC topical analgesics have limited effectiveness and duration in treating pain.
2. The currently available OTC topical analgesics may have socially embarrassing odors after application because of the strong scent of menthol, wintergreen (methyl salicylate), camphor, or strongly aromatic essential oils, etc.
3. The currently available OTC topical analgesics may contain staining or allergenic artificial dyes (e.g. blue or green) or synthetic perfumes.
4. The oil or fat contents (creams, salves and lotions, etc.) of the currently available OTC topical analgesics, or plant pigments or dyes in the currently available OTC topical analgesics may visibly stain clothing or leave greasy spots, or be allergenic and/or sensitizing to certain individuals.
5. The currently available OTC topical analgesics may contain substances that are irritating, allergenic, sensitizing, or toxic in excess or high concentrations that should not be applied more than 3 or 4 times daily, or are dangerous if ingested. Such products may contain ingredients that produce unpleasant or distracting physical sensations (counterirritants) such as stinging or burning from capsaicin (which may occur for several days), hot or cold sensations from menthol or wintergreen, or the possibility of allergic reaction to salicylate containing aspirin-like products (trolamine salicylate, methyl salicylate).
6. Some currently available homeopathic products are reported to have limited therapeutic indications (e.g. arnica tincture and 1x potency may produce toxic symptoms with open cuts or ingestion); and some higher potency (i.e. more serially diluted) homeopathic products do not appear to have strong or effective topical analgesic or anti-inflammatory properties.

An examination of existing OTC topical pain products in most pharmacies reveals, that although there are many brands to choose from, they all basically use various combinations of the same active ingredients, namely: menthol, methyl salicylate, camphor, and trolamine salicylate which have the drawbacks mentioned above. There is a need of novel formulations having analgesic and/or anti-inflammatory properties that can avoid the drawbacks of the prior art analgesic products. The homeopathic formulation of the present invention fulfill such a need. The formulations of the invention are not counterirritants and do not rely upon massage, heat, stimulation or counterirritation to allay pain. The formulations also do not require a trained classical homeopath to do casework diagnostics (costing significant time) to attempt to discover the similimum (remedy most resembling the patient's symptoms) and then attempt to prescribe correct potency, dosage and duration of action. When any of the formulations of the invention is used, no drug individualization using only one drug ingredient per dose for each person as practiced in classical homeopathy is required.

SUMMARY OF THE INVENTION

One of the aspects of the invention provides homeopathic formulations having analgesic and/or anti-inflammatory uses. The homeopathic formulation of the invention comprises (a) the tinctures and/or homeopathic preparations of at least 8 or 9 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*;

(b) the tincture and/or homeopathic preparation of *Bryonia Alba* and the tinctures and/or homeopathic preparations of at least 5, 6 or 7 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*;

(c) the tinctures and/or homeopathic preparations of at least 5, 6 or 7 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*, with the proviso that the formulation does not contain the tincture(s) and/or homeopathic preparation(s) of *Echinacea Augustifolia* and *Symphytum Officinale*; or (d) active ingredients and one or more inactive ingredients, wherein the active ingredients consist of the tinctures and/or homeopathic preparations of 5, 6 or 7 herbs selected from *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*.

In one of the embodiments of the homeopathic formulations of the invention, the formulation comprises the tinctures and/or homeopathic preparations of *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*. In another embodiment of the homeopathic formulations of the invention, the formulation comprises the tinctures and/or homeopathic preparations of *Bellis Perennis, Calendula Officinalis, Hamamelis*

*Virginiana, Arnica Montana, Hypericum Perforatum, Aconitum Napellus, Ledum Palustre, Bryonia Alba* and *Ruta Graveolens*.

Alternatively, the invention provides a homeopathic formulation comprising the tinctures and/or homeopathic preparations of *Bellis Perennis, Hamamelis Virginiana, Arnica Montana, Hypericum Perforatum, Aconitum Napellus, Ledum Palustre*, and *Ruta Graveolens*, but excluding the tincture(s) and/or homeopathic preparation(s) of *Echinacea Augustifolia* and *Symphytum Officinale*. The invention also provides a homeopathic formulation comprising the tinctures and/or homeopathic preparations of *Bellis Perennis, Arnica Montana, Hypericum Perforatum, Aconitum Napellus, Ledum Palustre*, and *Ruta Graveolens*, with the proviso that the formulation does not contain the tincture(s) and/or homeopathic preparation(s) of *Echinacea Augustifolia* and *Symphytum Officinale*. Within the scope of the invention is a homeopathic formulation comprising the tinctures and/or homeopathic preparations of *Bellis Perennis, Arnica Montana, Hypericum Perforatum, Aconitum Napellus*, and *Ruta Graveolens*, but excluding the tinctures and/or homeopathic preparation of *Echinacea Augustifolia* and *Symphytum Officinale*.

Yet another embodiment of the homeopathic formulations of the invention consists of the tinctures and/or homeopathic preparations of *Bellis Perennis, Hamamelis Virginiana, Arnica Montana, Hypericum Perforatum, Aconitum Napellus, Ledum Palustre*, and *Ruta Graveolens*, mixed with one or more inactive ingredients. Still another embodiment of the homeopathic formulations of the invention consists of, as active ingredients, the tinctures and/or homeopathic preparation of *Bellis Perennis, Arnica Montana, Hypericum Perforatum, Aconitum Napellus, Ledum Palustre*, and *Ruta Graveolens*, mixed with one or more inactive ingredients. The invention also provides a homeopathic formulation consisting of, as active ingredients, the tinctures and/or homeopathic preparations of *Bellis Perennis, Arnica Montana, Hypericum Perforatum, Aconitum Napellus*, and *Ruta Graveolens*, mixed with one or more inactive ingredients.

The homeopathic formulations are useful in treating pain and/or inflammation. Another object of the invention is a method of treating pain in a subject, preferably a subject in need of such treatment, which method comprises the step of administering a pain treating effective amount of a homeopathic formulation of the invention to the subject, wherein the subject is an animal. Preferably, the subject is a mammal. More preferably, the subject is a human. In the method, the homeopathic formulation is administered, preferably, topically.

Another object of the invention is a method of treating inflammation in a subject, preferably a subject in need of the treatment, which method comprises administering an anti-inflammatory amount of a homeopathic formulation of the invention to the subject, wherein the subject is an animal. Preferably, the subject is a mammal. More preferably, the subject is a human. In the method, the homeopathic formulation is administered, preferably, topically.

DETAILED DESCRIPTION OF THE INVENTION

In addition to the herbal active ingredients described above, the homeopathic formulations of the invention optionally further contain one or more physiologically acceptable carriers and/or excipients. An example of the physiologically acceptable carriers and/or excipients is purified, preferably sterile, water. The homeopathic formulations of the invention preferably are made in a clear gel base. Preferably, the clear gel base comprises water, glycerine (preferably, vegetable glycerine USP), a polyacrylic acid resin thickener (preferably, CARBOPOL 940), triethanolamine and methylparaben.

The homeopathic formulations of the invention solve the problems described above related to currently available OTC topical analgesics by effecting very fast pain and/or inflammation relief, as well as long duration of relief even after discontinuance of usage. Typically only a small amount, such as about 5-20 mg of the formulation per square inch of area to be treated (e.g. 10 mg/square inch), of the formulation is able to effectively treat a painful area, unlike currently available OTC topical analgesics which require far greater quantities. For most acute and chronic cases, analgesic relief is obtained within approximately 30 seconds to 2½ minutes after the first topical application, without massage, of a homeopathic formulation of the invention with an average pain-free duration of 8 hours (or longer duration, e.g. days to months, with one to multiple applications). The formulations of the invention can also offer pain relief after discontinuance even in chronic pain cases. The formulations of the invention can also treat even difficult pain problems (e.g., Lyme disease pain, migraine headaches, etc.) not normally considered topically treatable and also resolve many cases on a long term to permanent basis without socially embarrassing odors, redness, stains, greasiness; or unpleasant physical sensations such as stinging, itching, burning, cooling sensations, irritations, drying of skin, or numbness, found in many, if not most, currently known OTC topical analgesics or anti-inflammatory agents. The formulations of the invention preferably are made in a gel base.

The homeopathic formulations of the invention are not counterirritants and thus do not rely upon the principal of producing a less severe pain to counteract a more intense pain; and consequently these formulations are not required to incorporate menthol, camphor, methyl salicylate, or trolamine salicylate. The formulations of the invention can be novel homeopathic topical pain relief products preferably in a nearly clear gel base. Each of the formulations of the invention can be legally sold as a homeopathic OTC drug per the requirements of the Food and Drug Administration, or as a homeopathic prescription drug where lower potencies of certain ingredients such as Aconitum as specified in HPUS can only be sold on a prescription basis.

Each of the formulations of the invention can be applied as a small dab (e.g. about 100 mg) to the fingertip and lightly spread across approximately 10 square inches of skin surface over a painful area or inflammatory region. Massage or pressure is unnecessary for the therapy. The formulations of the invention are dry to touch in a few minutes leaving the skin smooth, moist and soft. A few chronic or difficult to treat conditions may require a second or third application of any of the formulations of the invention a few hours apart. There does not appear to be another OTC topical product in any category that can stop pain so quickly, and with such long lasting duration; that upon application is virtually "socially invisible", and feels pleasant and soothing during application. Furthermore, those unable to get relief from topical pain relievers often resort to oral aspirin and non-steroidal anti-inflammatory drugs which dramatically increase the risk of peptic ulceration and renal failure when used chronically—and increase the risk of drug interaction. Thus, because of unique topical effectiveness, the formulations of the invention may prevent many adverse internal reactions from unnecessary overuse of non-steroidal anti-inflammatory drugs.

In each of the formulations of the invention, there is a polypharmaceutical combination of individual herbal active ingredients that are botanically derived. Preferably, the herbal active ingredients of the formulations of the invention are prepared according to the Homeopathic Pharmacopoeia of United States (HPUS), with accepted methods of mother tincture preparation, and dilution and succusion to potentize such ingredients per HPUS instructions and requirements. Each herb of the formulations of the invention can be succussed 20 to 30 times per dilution. The herbal active ingredients in this formulation can be manufactured by a qualified homeopathic manufacturer following standard homeopathic industry guidelines, and preparation of active ingredients per HPUS procedures. The homeopathic active ingredient can then be combined with a base, preferably the unique gel base described below.

In this patent application, the terms "tincture" and "homeopathic preparation" of an herb refer to extracts of a part, combinations of parts and/or the entirety of the herb, with the exception that the "tincture" and "homeopathic preparation" of *Arnica Montana* refer to extracts of the whole *Arnica Montana* plant. The "tincture" can be prepared by exposing a part, parts and/or the entirety of the herb in a solvent, e.g. alcohol and/or water. The "tincture" of an herb preferably is a mother tincture of the herb prepared according to the procedures in HPUS. The "homeopathic preparation" can be prepared by dilution of the "tincture" with an appropriate liquid such as water or alcohol. The "homeopathic preparation" of an herb for the formulation of the invention is preferably prepared per HPUS procedures, wherein the mother tincture of the herb is serially diluted and subjected to succussion according to the target potency using potentization procedures known in the art of homeopathy. Also, herbal or unofficial preparations of the herbs may be used. For example, non-homeopathically prepared tincture, or dilution or infusions, or water or alcohol extracts, or powdered plasters, decoctions, poultices, etc., or any other methods of herbal preparations, or whole herbs whether impotentized or undiluted or not can be used as the herbal active ingredients in the formulations of the invention. As used herein, as per HPUS, the "tincture" and "homeopathic preparation" of *Arnica Montana* is defined differently in a separate HPUS monograph from an extract of "*Arnica Montana* radix," because the extract of "*Arnica Montana* radix," is prepared from the root of an *Arnica Montana* plant while the "tincture" and "homeopathic formulation" of *Arnica Montana* are prepared from the whole *Arnica Montana* plant.

The "potencies" given in Tables 1 and 2 below are as defined in HPUS. For instance, an active drug at a potency of 1× means that a tincture, preferably as defined in HPUS, of the active drug is diluted 1 in 10, e.g. 1 ml of the tincture is mixed with 9 ml of a diluent liquid, and then successed at least 10 times, according to known potentization procedures in homeopathy. A potency of 2× means that the active drug having a potency of 1× is further diluted 1 in 10 and then successed at least 10 times yielding the active drug at 2× potency. A potency of 3× means that the active drug having a potency of 2× is further diluted 1 in 10 and then successed at least 10 times yielding the active drug at 3× potency. In some of the homeopathic formulations of the invention, the active drugs can be 8 herbs selected from, or all 9 homeopathic herbs in, the list *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*. In yet some of the homeopathic formulations, the active drugs can be 5, 6 or 7 herbs selected from the list; *Bellis Perennis, Calendula Officinalis, Hamamelis Virginiana, Arnica Montana, Hypericum Perforatum, Aconitum Napellus, Ledum Palustre, Bryonia Alba* and *Ruta Graveolens*, with the proviso that the formulations do not contain the tincture(s) and/or homeopathic preparation(s) of *Echinacea Augustifolia* and *Symphytum Officinale*. The extracts of these herbs at the potencies disclosed below can be used as active ingredients which are mixed (optionally one or more other active ingredients, if allowed by the homeopathic formulation, and/or or more physiologically acceptable carriers and/or excipients may also be added), and then the mixture can be blended with other ingredients in a base to form a homeopathic formulation of the invention.

Potency and Dosage Variations of the Homeopathic Formulations:

In the homeopathic formulations of the invention, each of the herbal active ingredients can exist in the form of a tincture or diluted tincture preferably subjected to potentization based on procedures known in homeopathy, wherein the tincture is preferably as defined in HPUS for the particular herb. Examples of potency variations of the herbal active ingredients in the homeopathic formulations of the invention that can be used are shown in Table 1 below. In other words, if one of the herbal active ingredients in Table 1 is selected to be included in a homeopathic formulation of the invention, the extract of the particular herbal active ingredient at a potency that falls within the potency range listed in Table 1 for the particular homeopathic herbal active ingredient may be used to make the homeopathic formulation for the corresponding use, either external or internal. The potencies in Table 1 are presented as decimal potencies, which are preferred topically over centesimal, M or Q potencies because decimal potencies offer more potency gradations than centesimal, M or Q potencies, especially at lower potencies. Decimal potencies also generally receive twice as many energizing succesions as centesimal potencies of the same total dilution.

TABLE 1*

Potencies of Active Ingredients

| Active Ingredients | External Use Potency Range | Internal Use Potency Range |
|---|---|---|
| Bellis Perennis | Tinct.**–400× | 1×–400× |
| Calendula Officinalis | Tinct.–400× | 1×–400× |
| Hamamelis Virginiana | Tinct.–400× | 1×–400× |
| Arnica Montana | Tinct.–400× | 3×*–400× |
| Hypericum Perforatum | Tinct.–400× | 3×*–400× |
| Aconitum Napellus | 3×–400× | 3×*–400× |
| Ledum Palustre | Tinct.–400× | 1×–400× |
| Bryonia Alba | Tinct.–400× | 3×*–400× |
| Ruta Graveolens | Tinct.–400× | 3×*–400× |

*Note:
1× or 2× may also be used if the formulation of the invention is used as a prescription drug. However, care must be taken to prevent toxicity by correct dosing and/or avoiding allergic reaction, when formulating and prescribing. HPUS should be consulted.
**"Tinct." means mother tincture as per HPUS.
Decimal (x) potencies above may also be converted to centesimal potencies (e.g., 400×=200 C.). Potencies higher than 400× (200 C.), e.g. 1M, 10M or 50M, can also be used in the homeopathic formulations of the invention - either topically or internally. However, higher potencies will be more useful internally.

In the homeopathic formulations of the invention having the herbal active ingredients at potencies falling with the potency ranges listed in Table 1, each of the herbal active ingredients can be present in amounts expressed as percentage by weight of the finished homeopathic formulation that vary from about 0.1% to about 50%, preferably about 0.2% to about 20%, more preferably about 0.3% to about 10%, and even more preferably about 0.4% to about 8%, of the total weight of the formulations, For instance, if *Bellis Perennis* is used at a potency of 1×, the homeopathic formulation can contain about 0.1% to about 50% by weight of the 1× *Bellis Perennis*.

In some of the homeopathic formulations of the invention, the amounts of the herbal active ingredients can vary from 1% to 10% of drug tincture for external use in gel or other base. Higher percentages of tincture may be used up to about 50% before gels degrade. Equal amounts of the various homeopathic herbal active ingredients may be used, or some homeopathic herbal active ingredients may be supplied in multiple potencies. There is no advantage in varying the weight of each active ingredient within reason because homeopathic drugs operate on an energetic level, and are generally not dose dependent (except as internal LM potencies). Thus, twice as much of the effective resonant dose will not have twice a greater effect than the correct minimal dosage, as a basic concept in homeopathy is the efficacy of minimal dosing. According to the Avogadro's number, beyond 12C (24×) not one molecule of the original substance can be found in a formulation. Higher potencies than 200C (400×) can also be used. However, such potencies will have less local physiological effect and more of a psychological or systemic symptom effect and will be more useful internally. Multiple potencies of the same drug may also be used, e.g. *Arnica* 3×, 6× and 12×, etc., for a potency chord.

The homeopathic herbal active ingredients in the form of tinctures or diluted tinctures subjected to potentization are combined to form an active ingredient mixture. The active ingredient mixture can be supplied as 40% ethanol alcohol tincture, although more or less alcohol or water will not affect the analgesic effectiveness of the finished homeopathic formulation. The active ingredient mixture is then put in a base, preferably a clear gel base. Preferably, isopropyl alcohol or propylparaben should not be used in the homeopathic formulations of the invention.

If a clear gel base is used in some of the embodiments of the homeopathic formulations, the clear gel base may contain 1-99%, e.g. 8-10% or 50-99%, active ingredients by weight. However, other bases described may also be substituted for the gel base, and other gel bases can also carry the active ingredients (see "Other Topical Delivery Systems"), but without the same "social invisibility" emollient and soothing properties of the preferred gel base.

These embodiments of the homeopathic formulations of the invention can be prepared by blending 1-99%, e.g. 1-50%, of the active ingredients into 99-1%, e.g. 99-50%, clear gel base. The percentages may vary from these numbers if bases (e.g. liniment) other than a clear gel base are used. Preferably, violent agitation or high-speed blending should be avoided in order to prevent changing potencies of homeopathics. Also, any exposure to direct sunlight, higher temperatures, volatile organic compounds, x-rays, and electromagnetic fields should be avoided while processing, storing and shipping in order to prevent theoretical change or neutralization in potencies. All other appropriate delivery forms as mentioned in the HPUS, both internal and external, can be used to carry the active ingredients of the homeopathic formulation of the invention. Preferably, the homeopathic formulations are put in plastic, glass or other containers following HPUS, GMP's and all OTC regulations.

Each of the homeopathic formulations of the invention can be administered in standard homeopathic forms and dosages as determined by an individual seeking pain treatment who is knowledgeable about homeopathy or by a homeopathic practitioner. For external uses, the homeopathic formulation of the invention can be applied topically as needed, e.g. 1 to 6, preferably 1 to 4, times a day or every 30 minutes at the start of an injury for the first 2 hours. For instance, with each topical application, the homeopathic formulation can be applied in an amount sufficient to cover the skin of a painful area to be treated. For internal uses, the amount of the homeopathic formulation to be administered can be 2 to 4 pilules or tablets a day in weight standardized by a homeopathic pharmacy, e.g. according to homeopathic pharmaceutical necessities. With internal administration, the use of the formulation should be discontinued once pain and/or inflammation has stopped, according to classical homeopathic principles.

One of the Preferred Formulations of the Invention

Each 2 oz or 56.7 g of this preferred formulation contains 4.536 ml of an active ingredient mixture and 52.16 g of a clear gel base, wherein the active ingredient mixture contains 1.81 g ethanol. The components of the active ingredient mixture used to make the preferred homeopathic formulation are presented in Table 2, while the components of two alternative clear gel bases that could be used to make the preferred homeopathic formulation are presented in Table 3.

TABLE 2

Active Ingredient Mixture*

| HPUS Active Ingredients | Potency** | % by Weight*** |
|---|---|---|
| *Bellis Perennis* | 1× | 0.8889 |
| *Calendula Officinalis* | 1× | 0.8889 |
| *Hamamelis Virginiana* | 2× | 0.8889 |
| *Arnica Montana* | 3× | 0.4445 |
| *Arnica Montana* | 6× | 0.4445 |
| *Hypericum Perforatum* | 2× | 0.8889 |
| *Aconitum Napellus* | 3× | 0.8889 |
| *Ledum Palustre* | 3× | 0.8889 |
| *Bryonia Alba* | 6× | 0.4445 |
| *Bryonia Alba* | 12× | 0.4445 |
| *Ruta Graveolens* | 3× | 0.8889 |
| Total | | 8.000% |

*The active ingredient mixture is supplied as 40% ethanol alcohol tincture.
**The potency is as defined in HPUS.
***The percent by weight is based on the total weight of the homeopathic formulation of the invention. For instance, the finished homeopathic formulation contains 0.8889% by weight of a *Bellis Perennis* extract at a potency of 1× prepared as per HPUS.

TABLE 3

Clear Gel Base

| Ingredients* | Alternative 1 % by Weight** | Alternative 2 % by Weight** |
|---|---|---|
| Purified Water | 89.71% | 89.85% |
| Vegetable Glycerine (USP) | 0.92% | 0.92% |
| Carbopol 940 | 0.60% | 0.60% |
| Triethanolamine (Trolamine) | 0.40% | 0.40% |
| Methylparaben (NF) | 0.37% | 0.23% |
| Total | 92.00% | 92.00% |

*Preferably, no other ingredients are used in the clear gel base.
**The percent by weight is based on the total weight of the homeopathic formulation of the invention.

This embodiment of the preferred formulation can be made be gently blending 8% of the active ingredient mixture into 92% of the clear gel base. More preferably, precaution should be taken to avoid violent agitation or high-speed blending in order to avoid changing the potencies of the active ingredients, and also to avoid exposure to direct sunshine, high temperatures, volatile organic compounds, x-rays, and electromagnetic fields while processing and storing in order to prevent a theoretical change or neutralization of potency. Optionally, the formulation can be stored in a suitable plastic or glass container following Good Manufacturing Practices and all OTC regulations.

Variations of the Formula:

There are many possible variations of the preferred formulation of the invention that will also have good analgesic therapeutic properties, but have lesser efficacy and/or utility for reasons including: (1) Potential toxicity and/or allergic reaction when using lower potency (less diluted tincture and 1×) of *Arnica*, and/or *Ruta*, and/or *Aconitum*; and (2) lesser topical analgesic strength if just used in higher potencies such as 12× and higher. Although most homeopathic philosophical literature indicates that the higher dilutions and potentizations are more powerful when used "internally", the literature does not describe higher potency as being more powerful topically. However, the effectiveness of the preferred homeopathic formulation of the invention demonstrates that the lowest decimal potencies (1×, 2×, 3×) are more effective as an external topical analgesic when combined with slightly higher low potencies (6×, 12×) as the right combination of drugs with correct analgesic properties.

The homeopathic formulations of the invention can be varied in terms of the potency and dosage, or in terms of the ingredients. All requirements for manufacturing the other embodiments of the homeopathic formulations of the invention are the same as described for the preferred formulation.

Herbal Active Ingredient Variations of the Homeopathic Formulations:

The preferred homeopathic formulation of the invention comprises 9 different herbal active ingredients in 11 different potency variations (see Table 2). Some of the formulations of the invention can also be made by not using one of the 9 herbal active ingredients (e.g. see Variation #1 in Table 4 below). As one or some of the 9 herbal active ingredients is excluded from the formulations, the formulations still have powerful pain relieving and anti-inflammatory properties. The homeopathic formulation of the invention can comprise 7 herbal active ingredients (e.g. see Variation #2, Table 4), 6 herbal active ingredients (e.g. see Variation #3, Table 4) or 5 herbal active ingredients (e.g. see Variation #4, Table 4), with the proviso that the formulation does not contain any other active ingredient or the formulation does not contain the tincture(s) and/or homeopathic preparation(s) of *Echinacea Augustifolia* and *Symphytum Officinale*. However, each omission of an herbal active ingredient from the list of 9 slightly lessens the total product effectiveness. The potency and dosage ranges for both external and internal uses as well as the ranges of the amounts of the active ingredients in terms of percent by weight (based on the total weight of the homeopathic formulation) described above in the "Potency and Dosage Variations of the Homeopathic Formulation" subsection can also apply to the embodiments of the homeopathic formulations having herbal active ingredient variations described herein (Table 4). The homeopathic formulations containing the herbal active ingredient variations shown in Table 4 are all effective in treating pain and/or inflammation.

The above variations of herbal active ingredients may be used in any potency or dosage or percentage described in the subsection of "Potency and Dosage Variations of the Homeopathic Formulation" (e.g. see Table 1 for the potency examples). However, the potencies described in the preferred formulation are most effective (see Table 2).

Drug Delivery Methods:

Gels are the preferred vehicles of dispensing the homeopathic formulations of the invention. Gels are more accurately called jellies because they are compounds of water soluble ingredients, usually clear, of a uniform semisolid consistency. Gels maintain a uniformity that is useful in keeping active ingredients in the homeopathic formulations evenly dispersed in their aqueous base. Brownian motion builds up networks in gels and restores their shape when they have been ruptured by stresses (e.g. settling or shaking). The longer the dosage contacts the skin (i.e. nerve endings), the longer the duration of action. As the preferred formulation of the invention is in a gel base that soothes and smoothes the skin without socially objectionable odor, one is less likely to want to wash away the homeopathic formulation from the skin.

Other Topical Delivery Systems:

In addition to the preferred gel base, various other gel base formulations can carry the active ingredients in the homeopathic formulations of the invention with varying degrees of success. However, the use of glycerine and calendula (1×) and other homeopathics in a water gel base of the preferred formulation is very emollient, non-drying, and soothing to the skin. Other carrier bases may also be used to deliver the active ingredients topically such as: water, alcohol, water/alcohol, cream ointment, salves, lotion, liniment, tinctures, cream gel, lotion ointment, rub, spray, aerosol, lotion spray, balm rub, gel ointment, lotion cream, poultice, plaster, infusion, decoction and other herbal methods of preparation. However, the gel delivery system does work best.

Internal Use of the Homeopathic Formulations:

Any of the homeopathic formulations of the invention will also have similar pain relieving and/or anti-inflammatory properties when taken internally, but the specific local analgesic and/or anti-inflammatory action will not be as pronounced. The active ingredients of the homeopathic formulations may be used with any of the standard delivery systems used in oral homeopathy in any acceptable combination such as: tablets, drops, pills, sugar pills, water, glycerine, milk sugar and cane sugar vehicles, alcohol, medicated powders, medicated globules (pellets, pilutes), cones, etc. The delivery system is relatively unimportant. However, liquid systems will retain more volatile essences found in the low potency botanical tincture starting materials, and will contact more nerve endings in the mucosa.

The homeopathic formulations of the invention are also effective in treating pain and/or inflammation when administered parenterally, such as intravenously, or with any other

TABLE 4

Examples of Variation of Active Ingredients

| VARIATION #1 | VARIATION #2 | VARIATION #3 | VARIATION #4 |
|---|---|---|---|
| Bellis Perennis | Bellis Perennis | Bellis Perennis | Bellis Perennis |
| Calendula Officinalis | Hamamelis Virginiana | Arnica Montana | Arnica Montana |
| Hamamelis Virginiana | Arnica Montana | Hypericum Perforatum | Hypericum Perforatum |
| Arnica Montana | Hypericum Perforatum | Aconitum Napellus | Aconitum Napellus |
| Hypericum Perforatum | Aconitum Napellus | Ledum Palustre | Ruta Graveolens |
| Aconitum Napellus | Ledum Palustre | Ruta Graveolens | |
| Ledum Palustre | Ruta Graveolens | | |
| Ruta Graveolens | | | | method of homeopathic and/or herbal and/or allopathic drug administration, such as intramuscular injections. Furthermore, each of the homeopathic formulations of the invention can also be administered in suppository form (anal or vaginal) where the ingredients can be actively and quickly absorbed, and would have a strong systemic effect on pain. However, influence on local pain will be less pronounced and focused than local topical application of the homeopathic formulation, especially if the homeopathic formulation is made in a gel base. The formulation could also be taken nasally, or as eyedrops, or eardrops for pain and inflammation. It would, of course, have to be prepared in appropriate potency, and carried in a safe and effective base as, for example, described in OTC and HPUS literature.

Human Test Results:

A homeopathic formulation containing the herbal active ingredients of Table 2 in a clear gel base of Table 3 was administered to at least 47 human adult subjects having pain or pain associated with inflammation to test the effectiveness of the formulation in treating pain and/or inflammation. In the majority of the subjects, testing was conducted under physician supervision (see Table 5), while testing was done in the remaining 12 subjects not under physician supervision (see Table 6). The formulation was applied topically to the affected area of the body. For headaches, the formulation was applied to the cervical area and painful areas of the head. Except for 2 subjects, the formulation was found to be highly effective in treating pain and/or inflammation (see Tables 5 to 6).

Extremely rapid pain relief, within approximately 30 seconds to 2½ minutes of an initial application, was detected in most test cases of either acute or chronic pain. After the extremely rapid onset of pain relief, the degree of pain relief would keep increasing up to a maximum after about 10-40 minutes, depending on test subjects. Typically the first application would relieve most pain. In some of the test subjects having difficult-to-treat pain, total pain relief was achieved at 10 to 15 minutes. The formulation of the invention worked with a rapidity not previously described in the topical homeopathic, allopathic or OTC literature. The formulation was effective on both pain, e.g. arthritic pain or muscle sprains, traditionally treated by OTC analgesics, as well as difficult-to-treat non-typical pain, e.g. pain associated with Lyme disease, previously not described in the literature for the individual herbal active ingredients in the formulation tested.

One application of the formulation of the invention in most cases would yield about 4-16 hours of pain relief with an average of about 8 hours, enabling subject to get an extended period of uninterrupted rest and sleep. Thus, the homeopathic formulations of the invention are also effective in treating insomnia secondary to pain. This relief duration far exceeds the relief times of other OTC topical allopathic analgesics, as well as available homeopathic OTC topical and oral products. Clinical testing showed many cases of total or permanent local pain and inflammation relief after first application, with pain intensity scores dropping from 10 (the worst pain) to 5 or much less, and moving toward total pain resolution in many cases. Other subjects with pain not regarded as normally treatable by topical analgesics obtained significant long duration of pain relief with 1 or 2 or more applications of the formulation.

Effective broad spectrum relief, including difficult-to-treat cases, was achieved with the formulation. The formulation was found to be effective in treating pain and inflammation from Lyme disease, hematomas, degenerative joint disease, migraine headache, insect bites, carpal tunnel syndrome, facial neuralgia, vagal nerve irritation, neuritis from radiation burn, menstrual cramps, stomach pain from influenza, etc. The formulation was also found extremely effective against pain, such as rheumatism, arthritis, stiffness; neck and back injury; sprains, strains, etc., customarily treated not very effectively with some prior art topical analgesics. Many cases of acute and chronic pain, inflammations, edema, bruises and injuries were totally resolved or significantly relieved faster and better than any other topical therapy known.

The pain relief achieved with the formulation of the invention was long lasting in most cases. Pain relief was obtained even after discontinuance of the application of the formulation. Clinical testing showed many cases with a permanent resolution for both acute and long term chronic pain conditions. The formulation was found to be effective in several subjects having chronic pain of many years duration or bad tried various kinds of medical therapies without significant relief. For instance, in one case of 8 years right shoulder pain from Lyme disease, "permanent" relief within 3 minutes of first topical application of the formulation of the invention was obtained. Several test subjects achieved complete pain relief for months after discontinuance of the application of the formulation, even where pain was of months or years duration before the formulation was used. Such a result had not been known to be achievable with other topical agents in either OTC or prescription status. OTC topical analgesics (both homeopathic and allopathic) typically only offer very limited short term temporary relief. Often the sensitizing, e.g. menthol, or irritating, e.g. capsaicin, or allergenic, e.g. salicylate, nature of many OTC drugs prevent their long term usage because the side effects of the drug will warrant their discontinuance. In contrast, multiple applications of the homeopathic formulation of the invention over a long period, e.g. about 6 months to a year, are well accepted by the users with no apparent side effects. Multiple cases of localized "permanent" resolution, or vast improvement lasting several months, were observed with the formulation of the invention.

Treatments with the formulation of the invention also resulted in rapid anti-inflammatory effects. Typically, anti-inflammatory effects would start in approximately 30 seconds to 30 minutes after a topical application of the formulation of the invention depending on the cause. When using the formulation, many test subjects had range of motion restored in restricted joints. The formulation helped various cases of inflammation, swelling, redness, and edema of various causes. Cases of successfully treated inflammation included rheumatoid arthritic knees, Lyme arthritis pain, swollen knee, sprains, stiffness, blisters, tendonitis, insect bites (e.g. hornet bite), headaches associated with vagal nerve irritation, facial neuralgia, and neuritis from radiation burn.

The formulations of the invention have additional advantages over currently available OTC drugs. The formulations do not have strong odors or irritating effects as some of the OTC drugs, making the formulations more acceptable to users. Furthermore, currently available OTC drugs tend to lose their effectiveness upon repeated administrations. In contrast, the formulations of the invention do not exhibit any refractory period upon repeated administrations. The absence of reduced effectiveness upon repeated administrations makes the formulations especially effective in long term therapies of pain and/or inflammation.

TABLE 5

RESULTS OF CLINICAL TESTS CONDUCTED UNDER PHYSICIAN SUPERVISION
FOR PREVIOUSLY PHYSICIAN DIAGNOSED SYMPTOMS

| Test Subject[a] | Symptom Description | Subjective Pain Intensity[b] | Pain Duration Before Product Application | Pain Relief After Product Application | Duration of Pain Relief After Product Application[c] | Total Number of Product Applications[d] | Outcome After Discontinuance of Product Use |
|---|---|---|---|---|---|---|---|
| M/52 | Left elbow pain (post trauma) | 5 | 2 Hours | Within <60 seconds; complete relief in 5 min. | "Perm." | 1 | Pain free |
| F/53 | Migraine headache | 7 | 1 Hour | Within approx. 3 min.; complete relief & restful sleep | "Perm." | 1 | Pain free |
| F/72 | Left knee severe pain (Lyme disease) | 9 | 1 Year | Within approx. 2 min.; complete relief | "Perm." | 1 | Pain free |
| M/40 | Right shoulder pain | 6 | 6 Weeks | Within <1 min.; complete relief | 8 Hours | 1 | Pain returned gradually |
| F/38 | Fibromyalgia | 5 | 3 Years | Within <5 min.; moderate relief | 8 Hours | 1 | Pain returned gradually |
| F/55 | Fibromyalgia | 7 | 10 Years | No relief | N/A | At least 1 | N/A |
| M/61 | Right hand pain (Lyme disease) | 6 | 2 Years | Within <2 min.; moderate relief | "Perm." | 1 | Pain free |
| F/28 | Right foot insect bite | 6 | 1 Day | Within <30 seconds; total relief | "Perm." | 1 | Pain free |
| F/66 | Neck pain (degenerative joint disease) | 5 | 5 Years | Within <2 minutes; moderate relief | 24 Hours | 1 | 50% Pain relief |
| M/61 | Right knee pain (Lyme disease) | 7 | 2 Years | Within <5 minutes; near complete relief | 24 Hours | 1 | Loved product. Pain returned gradually |
| F/23 | Left flank pain (fibromyalgia) | 8 | 1 Year | Within <5 minutes; near complete relief | 10 Hours | 1 | Moderate, long-term pain relief |
| M/66 | Right Shoulder pain (Lyme disease) | 6 | 8 Years | Within <3 minutes; complete relief | "Perm." | 1 | Pain free |
| F/49 | Right carpal tunnel syndrome | 6–7 | 6 Month | Within <5 minutes; moderate relief | 8–10 Hours | 7 | Good improvement |
| F/48 | Rheumatoid arthritis | 7–8 | 1 Year | Within <5 minutes; near complete relief | 8–10 Hours. | 1 | Pain returned gradually |
| M/60 | Legs (babesiosis) | 4–5 | 1 Year | No relief | N/A | At least 1 | N/A |
| F/27 | Neck/shoulder pain (Lyme disease) | 6–7 | 2 Months | Within <1 minute; excellent relief | 24 Hours | 1 | Pain returned gradually |
| F/46 | Right knee pain (Lyme disease) | 7–8 | 2 Months | Within <60 seconds; excellent relief | "Perm." | 1 | Pain free |
| M/31 | Left wrist sprain | 6–7 | 1 Week | Within <60 seconds; excellent relief | 24 Hours | 1 | Moderate long term pain relief |
| F/60 | Left elbow pain (Lyme disease) | 7–8 | 6 Years | Within <3 minutes; moderate relief | 24 Hours | 1 | "Took the edge off" |
| F/81 | Right hip (babesiosis) | 8–9 | 3 Years | Within <2 minutes; 75% relief | 24 Hours | 1 | Pain returned gradually |
| M/51 | Pain in both knees (degen. joint disease) | 6–7 | 1 Year | Within <2 minutes; moderate relief | 12 Hours | 1 | Pain returned gradually |
| F/36 | Left ankle sprain | 7–8 | 2 Weeks | Within <1 minute; 90% better | 8 Hours | 1 | Pain returned gradually |
| F | Facial neuralgia | 1 | Multiple episodes | 50% Improved | 2 Weeks | One each on 2 office visits | — |
| F | Cervical spine pain | 5 | Intermittent | 50% Relief at 10 minutes | — | 1 | Increased range of motion |
| M | Vertex headache (vagal nerve irritation) | 5 | Constant | 15% Improved in 15 minutes | — | At least 1 | — |

TABLE 5-continued

RESULTS OF CLINICAL TESTS CONDUCTED UNDER PHYSICIAN SUPERVISION
FOR PREVIOUSLY PHYSICIAN DIAGNOSED SYMPTOMS

| Test Subject[a] | Symptom Description | Subjective Pain Intensity[b] | Pain Duration Before Product Application | Pain Relief After Product Application | Duration of Pain Relief After Product Application[c] | Total Number of Product Applications[d] | Outcome After Discontinuance of Product Use |
|---|---|---|---|---|---|---|---|
| Same subject as above | Vertex headache (vagal nerve irritation) | 5 | Constant | 45% Improved over a week | — | At least 1 | — |
| F | Pain in right upper extremity rhomboids & trapezius bilateral, left scapula | 10 | Constant | 20% Relief in 3 minutes; 25% relief in 4 minutes | — | 1 | — |
| F/31 | Chronic migraine headache | 9 | 1 Day | 50% Relief in 20 min. with 1 application; 80% relief in 30 mins. with 2nd application | — | 2 | — |
| Same subject as above | One recurrence of headache | 5 | — | 100% Relief in 10 mins. | — | 1 | — |
| M | Muscle strain/sprain in right flank quadriceps; tendonitis in right knee | 10 | Constant | After 8 days muscle strain lessened by 75% at right flank; pain lessened by 50% in right knee | — | Multiple | Right flank pain intermittent |
| Same subject as above | Stiffness and pain in quadriceps; tendonitis; clicking right knee | 5 | Intermittent | 10% Relief in 15 minutes | — | Multiple | Continued to use product |
| M | Right lower rib cage, 1. Intercostal neuritis 2nd radiation burn | 10 | 10 Days | 50% Relief in 10 minutes; 60% relief with 2nd application | — | 2 | — |
| F/52 | Acute right ankle sprain/strain; right forearm bruise & hematoma; left upper arm bruise & hermatoma | 10 | Acute injury | Relief started within 5 minutes; 40% relief after 35 minutes | 1 Hour | 1 | — |
| Same subject as above | — | 1 | — | Bilateral upper extremities pain 95% resolved; edema 90% resolved | 3 Weeks | Multiple, at least twice daily | Minimal pain & discomfort |
| F/72 | Pain in left trapezius, left teres minor, left supra & infraspinatus muscles | Moderate to severe | 4 Months | 40% Improved after about 10–20 minutes | — | 1 | — |
| F/74 | Shooting pain in right wrist with muscles weakness, unable to lift objects | 10 | 2 Days | 50% Improved after 10 minutes | — | 1 | — |
| F/95½ | Bilateral knee pain | 5–10 | 4 Days | 45% Improved after 10–20 minutes | — | At least 1 | — |
| M | Supraspinatus tendonitis right shoulder, right flexor & extensor muscles | 10 at start | Persistent for 2–3 months | 10% Relief in 8 minutes; pain dropped to intensity level 4 after 23 applications | — | 23 | Continued to use product |

TABLE 5-continued

RESULTS OF CLINICAL TESTS CONDUCTED UNDER PHYSICIAN SUPERVISION
FOR PREVIOUSLY PHYSICIAN DIAGNOSED SYMPTOMS

| Test Subject[a] | Symptom Description | Subjective Pain Intensity[b] | Pain Duration Before Product Application | Pain Relief After Product Application | Duration of Pain Relief After Product Application[c] | Total Number of Product Applications[d] | Outcome After Discontinuance of Product Use |
|---|---|---|---|---|---|---|---|
| M | Muscle spasms bilateral lower extremities pitting edema | 5 | — | 50% Reduction in pain | — | 2 | — |

[a] M = male, F = female/years of age if known.
[b] Pain intensity scale from 1 to 10: 1 = barely noticeable, 5 = moderate, 10 = unbearable.
[c] "Perm." stands for permanent pain relief at time of study.
[d] Where physicians did not specify the total number of applications, "at least 1" was implied.

TABLE 6

RESULTS OF TESTS DONE BY INDIVIDUALS FOR TREATMENT OF SYMPTOMS

| Test Subject[a] | Symptom Description | Subjective Pain Intensity[b] | Pain Duration Before Product Application | Pain Relief After Product Application | Duration of Pain Relief After Product Application[c] | Total Number of Product Applications | Outcome After Discontinuance of Product Use |
|---|---|---|---|---|---|---|---|
| F/36 | Insomnia caused by neck & shoulder stiffness from stress | 8 | 3 Hours, nightly | 100% Relief from insomnia each night | 8 Hours of relief from insomnia and pain | 8 | Pain much reduced; rarely had to be treated daily; one treatment per week now suffices |
| F/55 | Head & neck pain | 10 | Hours | 100% Relief in about 4 minutes | Days | 6 | Continued to use as needed |
| F/55 | Insomnia from shoulder & neck pain with lumps | 8 | 2–3 Hours | 100% Relief from insomnia in about 20 minutes | Daily | 20 | Continued to use as needed |
| M/54 | Blisters on hands from friction | 5 | 2 Hours | 90% Relief | 8 Hours | 3 | No pain on 2$^{nd}$ day; complete healing |
| F/68 | Back injury, whiplash | 6 | 10 Years | 90% Relief | 4 Days | 8 | Great improvement; some pain remained |
| F/59 | Stomache pain/flu | Moderate to High | Constant | 90% Relief in about 1 minute | 4–8 Hours | 6 | Stomach flu pain stopped |
| F/87 | Chronic back pain | High | Constant | — | 6–8 Hours | Multiple | 85% Relief after 6 months |
| F/58 | Migraine headache, temporomandibular joint syndrome | Severe | 3 Days | 100% Relief in about 5 minutes | Constant | About 50 | Symptom free in 6 months |
| F/77 | Swollen knee with knots | High | Constant | 95% Relief in about 15 minutes | 4–6 Hours | 50 | Highly improved |
| M/56 | Right broken leg | High | 2 weeks | 80% Relief in about 15 minutes | 2–4 Hours | About 120 | Walking 2 weeks earlier than doctor's prognosis, speeded healing time in half |
| M/59 | Hornet bite, neck | Sharp shooting | A few minutes | Pain stopped in a few seconds | "Perm." | 2 or 3 | No recurrence of pain; no inflammation |
| Same subject as above | Rheumatoid arthritic knee, swelled every day, uncomfortable to walk | 5–6 | Every day for 3 years | Pain stopped by about 90%; swelling reduced by 90% | Up to 4 hrs | Multiple | Can go days without treating |
| F/53 | Stomach cramps (menstrual) | 5 | 10 Minutes | 100% Relief in 5 minutes | "Perm." | 1 | No further cramping during rest of cycle |

[a] M = male, F = female/years of age if known.
[b] Pain intensity scale from 1 to 10: 1 = barely noticeable, 5 = moderate, 10 = unbearable.
[c] "Perm." stands for permanent pain relief at time of study.

The invention claimed is:

1. A formulation comprising herbal active ingredients, wherein the herbal active ingredients comprise a tincture and/or homeopathic preparation of Bryonia Alba and the tinctures and/or homeopathic preparations of at least 5, 6 or 7 of *Bellis Perennis, Calendula Officinalis, Hamamelis Virginiana, Arnica Montana, Hypericum Perforatum, Aconitum Napellus, Ledum Palustre*, and *Ruta Graveolens*.

2. The formulation of claim 1, the herbal active ingredients comprising the tincture and/or homeopathic preparation of *Bryonia Alba* and the tinctures and/or homeopathic preparations of at least 6 or 7 of *Bellis Perennis, Calendula Officinalis, Hamamelis Virginiana, Arnica Montana, Hypericum Perforatum, Aconitum Napellus, Ledum Palustre*, and *Ruta Graveolens*.

3. The formulation of claim 2, the herbal active ingredients comprising the tincture and/or homeopathic preparation of *Bryonia Alba* at a potency ranging from tincture-400× and the tinctures and/or homeopathic preparations of at least 6 or 7 of *Bellis Perennis* at a potency ranging from tincture-400×, *Calendula Officinalis* at a potency ranging from tincture-400×, *Hamamelis Virginiana* at a potency ranging from tincture-400×, *Arnica Montana* at a potency ranging from tincture-400×, *Hypericum Perforatum* at a potency ranging from tincture-400×, *Aconitum Napellus* at a potency ranging from 3×-400×, *Ledum Palustre* at a potency ranging from tincture-400×, and *Ruta Graveolens* at a potency ranging from tincture-400×.

4. The formulation of claim 1, further comprising a gel base comprising water, glycerine, a polyacrylic acid resin thickener, triethanolamine and methylparaben.

5. The formulation of claim 2, further comprising a gel base comprising water, glycerine, a polyacrylic acid resin thickener, triethanolamine and methylparaben.

6. The formulation of claim 1, wherein the formulation is a topical formulation.

7. The formulation of claim 6, the herbal active ingredients comprising the tincture and/or homeopathic preparation of *Bryonia Alba* at a potency ranging from tincture-400× and the tinctures and/or homeopathic preparations of at least 5, 6 or 7 of *Bellis Perennis* at a potency ranging from tincture-400×, *Calendula Officinalis* at a potency ranging from tincture-400×, *Hamamelis Virginiana* at a potency ranging from tincture-400×, *Arnica Montana* at a potency ranging from tincture-400×, *Hypericum Perforatum* at a potency ranging from tincture-400×, *Aconitum Napellus* at a potency ranging from 3×-400×, *Ledum Palustre* at a potency ranging from tincture-400×, and *Ruta Graveolens* at a potency ranging from tincture-400×.

8. The formulation of claim 6, further comprising a gel base comprising water, glycerine, a polyacrylic acid resin thickener, triethanolamine and methylparaben.

* * * * *